United States Patent
Aaron

(10) Patent No.: US 7,842,089 B2
(45) Date of Patent: Nov. 30, 2010

(54) INTERVERTEBRAL DISC PROSTHESIS

(75) Inventor: Alain Aaron, Quimper (FR)

(73) Assignee: Fournitures Hospitalieres Industrie-F.H. Industrie (FR)

( * ) Notice: Subject to any disclaimer, the term of this patent is extended or adjusted under 35 U.S.C. 154(b) by 0 days.

(21) Appl. No.: 10/583,316

(22) PCT Filed: Dec. 17, 2004

(86) PCT No.: PCT/FR2004/003295

§ 371 (c)(1),
(2), (4) Date: Mar. 29, 2007

(87) PCT Pub. No.: WO2005/065595

PCT Pub. Date: Jul. 21, 2005

(65) Prior Publication Data

US 2007/0276495 A1    Nov. 29, 2007

(30) Foreign Application Priority Data

Dec. 22, 2003    (FR) .................................. 03 15177

(51) Int. Cl.
*A61F 2/44* (2006.01)
(52) U.S. Cl. .................................. 623/17.16
(58) Field of Classification Search .... 623/17.11–17.16
See application file for complete search history.

(56) References Cited

U.S. PATENT DOCUMENTS

| | | | | |
|---|---|---|---|---|
| 4,759,769 A | * | 7/1988 | Hedman et al. .......... | 623/17.13 |
| 5,674,294 A | * | 10/1997 | Bainville et al. ......... | 623/17.16 |
| 6,582,468 B1 | * | 6/2003 | Gauchet .................. | 623/17.16 |
| 2003/0074067 A1 | * | 4/2003 | Errico et al. ............. | 623/17.14 |
| 2004/0193273 A1 | * | 9/2004 | Huang ..................... | 623/17.12 |

FOREIGN PATENT DOCUMENTS

| | | |
|---|---|---|
| FR | 2 709 949 | 3/1995 |
| FR | 2 723 841 | 3/1996 |
| FR | 2 734 148 | 11/1996 |

OTHER PUBLICATIONS

Barrans, Jr., Richard E.; "Liquids, Solids, and Compressibility"; Sep. 30, 2002.*
International Search Report; PCT/FR2004/003295; May 6, 2005.

* cited by examiner

*Primary Examiner*—Eduardo C Robert
*Assistant Examiner*—Elana B Fisher
(74) *Attorney, Agent, or Firm*—Cantor Colburn LLP

(57) ABSTRACT

The invention relates to an intervertebral disc prosthesis comprising two half-shells (7, 10) clasping a compression pad. According to the invention, the central part of one (10) of the two half-shells comprises a shaft (14) which faces the other half-shell (7), while the central part of said second half-shell (7) comprises a stud (13) which faces the first half-shell, said stud having a smaller cross-section than that of the shaft and being inserted therein. The sum of the lengths of the shaft (14) and the stud (13) is greater than the distance between the two half-shells (7, 10), the aforementioned compression pad being disposed between the two half-shells in the space between the shaft and the stud.

20 Claims, 3 Drawing Sheets

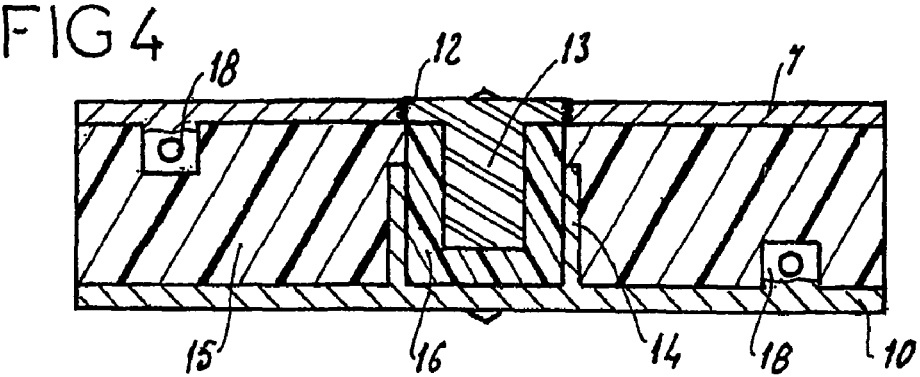
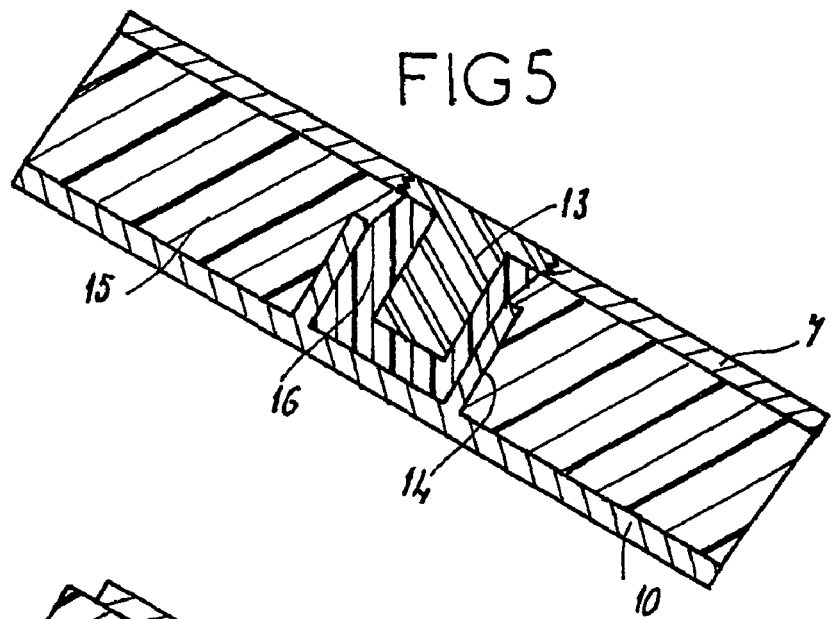
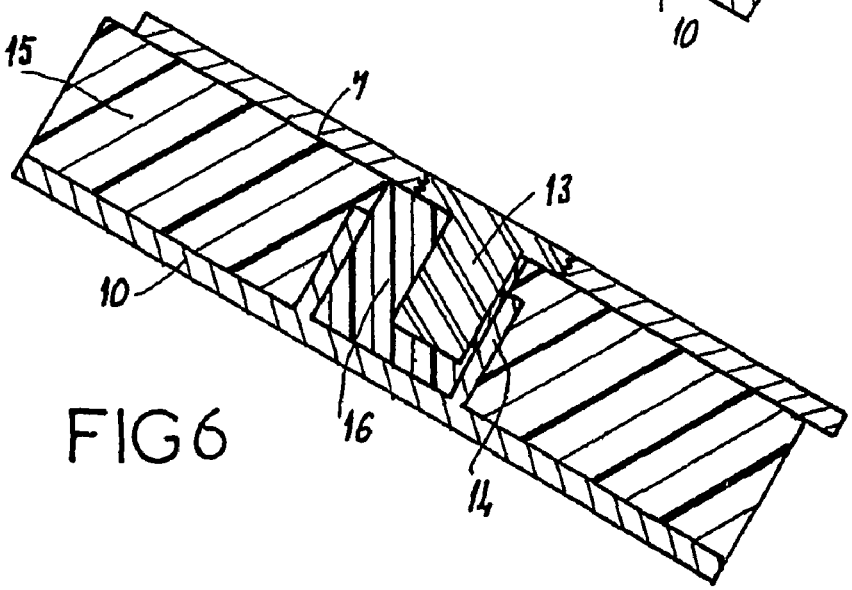

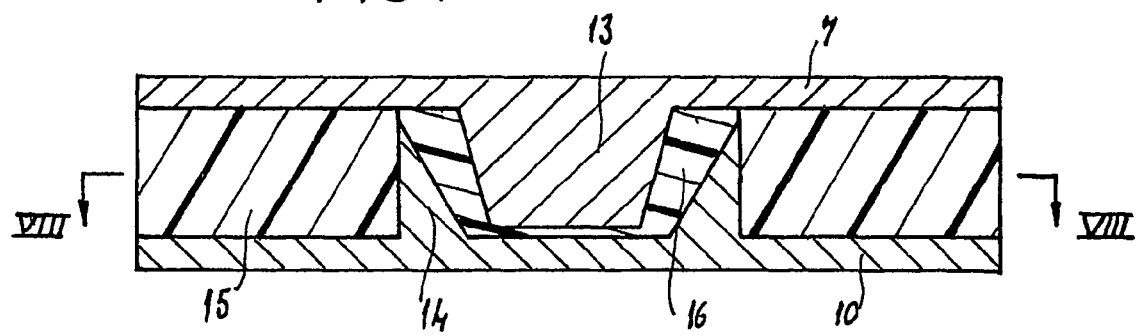
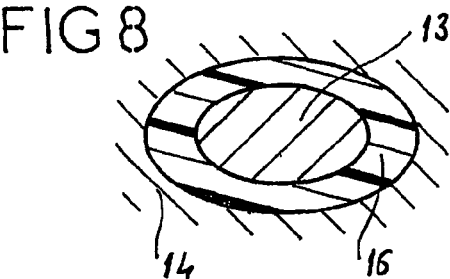

INTERVERTEBRAL DISC PROSTHESIS

TECHNICAL FIELD OF THE INVENTION

The present invention relates to a prosthesis designed to replace a damaged intervertebral disc of the spinal column.

It has an application in the field of orthopedic surgery.

BRIEF DESCRIPTION OF RELATED ART

The spinal column is composed of a set of superposed vertebrae that are connected to one another by fibro-cartilaginous discs called intervertebral discs. These intervertebral discs play a fundamental role in the statics and dynamics of the spinal column: they ensure the mobility of the vertebrae relative to one another.

These intervertebral discs are often subject to disorders associated with compression of the vertebrae, a herniated disc, a displacement of the vertebrae, or arthritic intervertebral degeneration. These disorders are very often the cause of pain or of functional problems that do not respond to medical treatment; in some cases, they can even be debilitating.

The method used to manage patients afflicted by these disorders generally involves a surgical intervention. Several surgical techniques are presently known.

The first technique involves simple excision of the disc; the damaged zone of the intervertebral disc is simply removed, which in turn suppresses the normal biomechanics of the disc. The two vertebrae adjacent to this disc then have reduced mobility relative to one another. In addition, such excision does not provide a definitive remedy to the patient's pain, since the damage to the disc may continue to worsen.

The second surgical technique involves intervertebral arthrodesis, by which the two vertebrae adjacent to the damaged disc are fused. This method does indeed provide a definitive remedy that blocks the development of the arthrosis, that is to say the degeneration of the disc. The main disadvantage of this method is that it suppresses all mobility of the disc.

The third technique, and presently the most common one, involves intervertebral arthroplastic surgery to replace the damaged disc by a prosthesis. Numerous types of prosthetic discs are known and are described in the work entitled "The Artificial Disc" edited by Mario Brock, H. Mickael Mayer and Klaus Weigel and published by Springer Verlag, 1991.

According to this work, the known prosthetic discs can be classed in two main categories:

The prostheses for which the fibrous part of the natural disc is preserved and used as a shell for the prosthesis. The inner core of the natural disc is then replaced either by a polymerizing product injected into the shell, or by elastic components introduced into the shell, or by a pouch inserted into the shell and inflated by means of a liquid or a polymer. Such a prosthesis is described in particular in the documents U.S. Pat. No. 4,772,287 and EP-A-0 277 282. The main difficulty in producing such a prosthesis lies in the fact that it is necessary to recover the geometry and compression resistance of the natural disc. In addition, such a prosthesis cannot be considered as a definitive remedy for the patient, since the preserved fibrous part of the disc may continue to deteriorate.

The completely artificial prostheses which replace a natural disc that has been completely removed.

A first technique for producing these completely artificial prostheses consists in introducing a sliding articulation between the two vertebrae. This articulation can be in direct contact with the vertebral plates; it can also consist of a ball centered as described in the document FR-A-2 372 622. Such a prosthesis with a centered ball has the disadvantage that the displacement of one vertebra relative to another causes friction in the area of the ball. This friction can produce irritation quite quickly and, after a certain length of time, can generate migrating pieces of debris caused by wear. This debris can produce a foreign-body reaction which, if it occurs in contact with the vertebral canal, can be the source of neurological problems.

A second technique for producing completely artificial prostheses consists in using a deformable architecture which is rigidly connected to the adjacent vertebral plates. Such a prosthesis is described, for example, in the document FR-A-2 124 815. This prosthesis consists more precisely of an element simulating the shape of an intervertebral disc and made of an elastomer material of the silicone type. Its disadvantage is that it provides only limited mobility of the adjacent vertebrae, its ability to deform being relatively limited. In addition, this prosthesis does not prohibit the radial expansion of the elastomer material under the stresses that are exerted on the prosthesis, and this is manifested in a risk of herniation to the vertebral canal.

Document FR 2 709 949 concerns an intervertebral disc prosthesis comprising two half-shells in the form of cups which are each fixed to one of the two vertebrae adjacent to the vertebral disc that is to be replaced, and between them is arranged a compression pad made of at least two materials, the pad being surrounded by a strap.

Such a prosthesis has the disadvantage of a lack of reliability on account of the risks of separation of the pad and the cups under the effect of the shearing forces that are exerted between the pad and the cups, in particular when the prosthesis is in an inclined position relative to the horizontal, under the conditions of use.

The rubbing of the pad against the strap can generate wear particles which lead to neurological disorders. In addition, the separation of the pad from the cups also leads to a risk of displacement of this pad, which can come into conflict with vital parts.

The technical problem on which the invention is based is that of producing an intervertebral disc prosthesis which is of a simple design and compact structure and which is perfectly safe to use, particularly by avoiding risks of separation of different component parts of the prosthesis, especially under the effect of shearing stresses.

BRIEF SUMMARY OF THE INVENTION

To this end, the intervertebral disc prosthesis to which the invention relates, comprising two rigid half-shells in the form of cups or plates which are each intended to be fixed to one of the two vertebrae adjacent to the intervertebral disc to be replaced, the two half-shells enclosing a compression pad made of at least two materials of different hardness, is characterized in that one of the two half-shells comprises, in its central zone, a shaft which is oriented toward the other half-shell, the second half-shell comprising, in its central zone, a stud whose cross section is smaller than that of the shaft and which is oriented toward the first half-shell and is engaged in the shaft of the latter, the sum of the lengths of the shaft and of the stud being greater than the distance between the two half-shells, the compression pad being disposed between the two half-shells, including within the volume situated between the shaft and the stud.

This structure allows the prosthesis to perfectly withstand the shearing stresses, since these are no longer absorbed, as is usually the case, solely by the interfaces between the compression pad and the cups, with subsequent risk of separation, but also by compression between the central stud and the wall of the shaft. In addition, it should be noted that in the event of tearing at the interface between the pad and one of the two half-shells, safety is afforded by the fact that the pairing of stud and shaft will limit the relative displacement of the two rigid half-shells.

Advantageously, the volumes disposed outside and inside the shaft, respectively, are filled with compressible materials of different hardness, the compressible material situated outside the shaft being harder than the material situated inside the shaft. This is because the material situated outside the shaft has to absorb the compression forces due in particular to the weight of the body and the rotation forces during movements of the body. This material scarcely deforms under high loads. By contrast, the material situated inside the shaft has a lesser hardness and is slightly compressible in volume, with a reduced deformation under a reduced load.

Advantageously, the compressible material situated outside the shaft has a Shore A hardness of between 60 and 100, and preferably of 80, while the compressible material situated inside the shaft has a Shore A hardness of between 25 and 30, and preferably of 28.

According to one embodiment of this prosthesis, the compressible material situated outside the shaft is a synthetic material of the polycarbonate urethane type, and the compressible material situated inside the shaft can in particular be formed by a mixture of two-component silicone elastomer, crosslinking at ambient temperature, and of an encapsulating copolymer whose blowing agent is isobutane. It should be noted that polyurethane has excellent biostability properties. The two half-shells or plates are made of a titanium-based alloy, and they each comprise, on their outer face, points intended to promote their fixation to a vertebra, and, on their inner face, lugs for attachment of the compression pad.

According to an advantageous characteristic of the invention, the stud projecting from a half-shell is fixed by being screwed into a through-hole in the latter.

A method for producing this prosthesis involves placing the two half-shells in a mold, with the stud withdrawn, injecting the material of greater hardness into the volume outside the shaft, pouring the material of lesser hardness into the volume inside the shaft via the opening which is formed in the half-shell and is intended to receive the stud, and then fixing the stud in place by screwing.

The opening formed in the outer half-shell is occluded by the stud, which is fixed by screwing before the end of crosslinking of the elastomer, which thus ensures it is impossible for the screw to come loose within the human body. It should also be noted that the outer material adheres to the titanium plate, ensuring sufficient leaktightness to permit pouring of the material situated inside the shaft, without loss of material.

BRIEF DESCRIPTION OF THE DRAWINGS

The invention will in any case be fully understood from the following description in which reference is made to the attached diagrammatic drawings which show, as non-limiting examples, two embodiments of this prosthesis.

FIG. 4 is a view thereof in transverse section through another plane.

FIGS. 5 and 6 are two views of this prosthesis under shearing stresses, in a case in which it is functioning normally and in a case involving tearing of an interface, respectively.

FIG. 7 is a view, similar to FIG. 2, of another prosthesis.

FIG. 8 is a cross-sectional view of this prosthesis along the line VIII-VIII in FIG. 7.

DETAILED DESCRIPTION OF THE INVENTION

Figure 1:
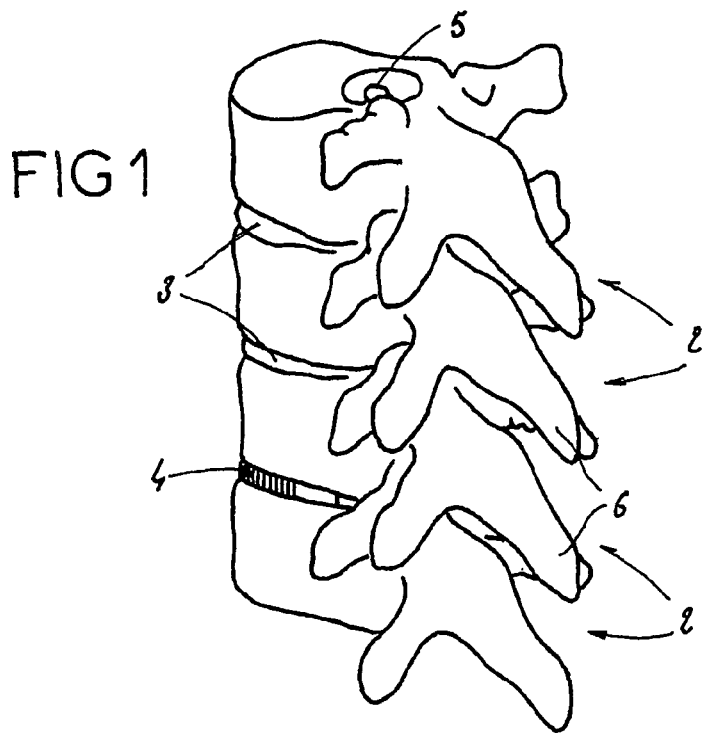
FIG. 1 is a perspective view of a portion of the spinal column including a prosthesis according to the invention.

FIG. 1 of the attached drawing shows a segment of the spinal column, more specifically illustrating four vertebrae 2, the three upper vertebrae being connected by two intervertebral discs 3, and the two lower vertebrae being connected by an intervertebral prosthesis 4. This figure also shows the vertebral canal 5 filled with spinal cord, and the spinous processes 6.

Figure 3:
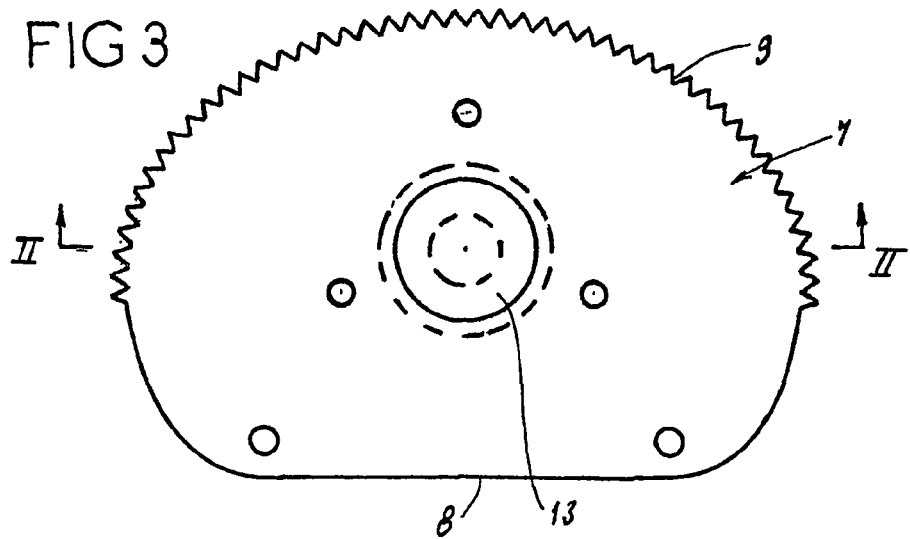
FIG. 3 is a plan view of this prosthesis.

FIG. 3 shows an intervertebral prosthesis in a front view. In this figure, a plate 7 can be seen which is a constituent part of the prosthesis and which is made of titanium alloy and has a substantially rectilinear side 8, and a curved side 9 with a toothing. This toothing makes it easier for the practitioner to maneuver the prosthesis when fitting it in place.

Figure 2:
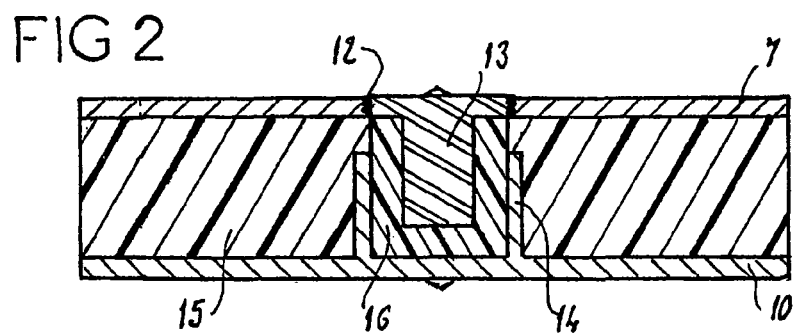
FIG. 2 is a view in transverse section, and on an enlarged scale, of this prosthesis along the line II-II in FIG. 3.

The prosthesis is better illustrated in FIG. 2. This prosthesis comprises an upper plate 7 and a lower plate 10 which are made of a titanium-based alloy. The upper plate 7 comprises, at its center, an internally threaded opening 12 allowing a threaded cylindrical stud 13 to be fitted by screwing. The plate 10 for its part comprises, in its central zone, a shaft 14 of circular cross section projecting toward the plate 7. The cumulative length of the stud 13 and of the shaft 14 is greater than the distance between the two plates 7 and 10. A pad of compressible material is disposed between the two plates 7 and 10. This pad, made in two parts, comprises a first material 15 disposed outside the shaft 14 and made of a harder compressible material than a compressible material 16 disposed inside the shaft, filling the space between it and the stud 13.

As can be seen from FIGS. 2 through 4, the plates 7 and 10 comprise, on their outer faces, points 17 which are intended to promote fixation to the vertebrae against which the plates are in contact. In addition, as is shown in FIG. 4, the plates 7 and 10 comprise, on their inner faces, that is to say on their faces directed toward one another, lugs 18 which promote attachment of the compressible damping material 15.

It should be noted that the compressible material 15 can be a synthetic material of the polyurethane type, while the material 16 can be formed by a mixture of two-component silicone elastomer, crosslinking at ambient temperature, and of an encapsulating copolymer whose blowing agent is isobutane.

FIGS. 5 and 6 show the prosthesis during its functioning, and in particular in the case of inclined functioning, which is normal on account of the location of certain prostheses. It will be seen from FIG. 5 that there is, on the one hand, a shearing movement between the compressible materials and the plates, but also a phenomenon of compression of the material 16 between the shaft 14 and the stud 13. This compression effect makes it possible to limit the effects of the shearing, and in particular to avoid separation between the compressible material 15 and one or other of the plates.

FIG. 6 shows the extreme case of tearing of the interface between the compressible material 15 and the upper plate 7. It is interesting to note that even in this extreme hypothetical situation, total separation of the various components does not occur, because the stud 13 comes to bear against the shaft 14, with interposition of a certain amount of material, which thus avoids any risk to the patient.

FIGS. 7 and 8 show an alternative embodiment of this prosthesis in which the same elements are designated by the same references as before. In this case, the stud 13 and the shaft 14 have a trapezoidal cross section, in longitudinal section, the cross section of the stud diminishing toward its free end. In addition, seen in transverse section, the stud 13 and the shaft 14 have a non-circular cross section, for example in the shape of an ellipse, in order to prevent a relative rotation of the two half-shells 7, 10 or of the compressible material 15.

In all cases, it is advantageous for the outer surfaces of the half-shells to comprise a coating of hydroxyapatite or creation of micro-porosities.

As will be evident from the above, the invention affords a considerable improvement to the existing technology by making available an intervertebral prosthesis of simple and compact structure which, in view of its structure, can be made with materials and in particular with plates of reduced thickness, while at the same time having excellent stability and excellent reliability.

It will be appreciated that the invention is not limited to the embodiments of this intervertebral prosthesis that have been described above by way of example, and that instead it encompasses all variants thereof. In particular, the compressible materials could be different, the stud of the upper plate could be non-removable, or the plates could have a cup shape instead of a plane shape, without thereby departing from the scope of the invention.

The invention claimed is:

1. An intervertebral disc prosthesis comprising:
   two plate-shaped or cup-shaped rigid half-shells, each of the half shells being configured to be fixed to one of two vertebrae adjacent to an intervertebral disc to be replaced, the two rigid half-shells being disposed on respective sides of a compression pad and affixed thereto; and
   a first of said two half shells comprising, in a central zone thereof, a hollow shaft oriented toward a second of said two half shells, the second half-shell comprising, in a central zone thereof, a stud oriented toward the first half-shell and penetrating into the hollow shaft, the compression pad including a core portion operatively engaged between and in contact with the hollow shaft and the stud, and an outer ring portion disposed outwardly of the core portion and of the hollow shaft, wherein the outer ring portion comprises a first surface and a second surface opposed to the first surface, the first and second surfaces of the outer ring portion being respectively affixed to inner surfaces of the two half-shells.

2. The prosthesis as claimed in claim 1, wherein the outer ring portion of the compression pad is harder than the core portion of the compression pad.

3. The prosthesis as claimed in claim 2, wherein the outer ring portion is made of a polycarbonate urethane type material.

4. The prosthesis as claimed in claim 1, wherein the core portion is cup-shaped.

5. The prosthesis as claimed in claim 1, wherein said compression pad includes another portion disposed between a free end of the hollow shaft and the second half-shell.

6. The prosthesis as claimed in claim 1, wherein the hollow shaft and the stud define an interior space between them, and wherein the core portion fills the interior space defined between the hollow shaft and the stud.

7. The prosthesis as claimed in claim 1, wherein the outer ring portion has a Shore A hardness of between 60 and 100.

8. The prosthesis as claimed in claim 1, wherein the core portion has a Shore A hardness of between 25 and 30.

9. The prosthesis as claimed in claim 1, wherein the core portion is made of a two-component silicone elastomer crosslinked at ambient temperature, and an encapsulating copolymer whose blowing agent is isobutane.

10. The prosthesis as claimed in claim 1, wherein the two half-shells are made of a titanium-based alloy.

11. The prosthesis as claimed in claim 1, wherein each half-shell comprises, on an outer face, pointed portions intended to promote its primary fixation to a vertebra.

12. The prosthesis as claimed in claim 1, wherein each half-shell comprises, on an inner face, lugs for attachment of the compression pad.

13. The prosthesis as claimed in claim 1, wherein the stud is threadedly engaged in a through-hole in the second half-shell.

14. The prosthesis as claimed in claim 1, wherein the stud and the shaft have trapezoidal cross sections.

15. The prosthesis as claimed in claim 1, wherein the stud and the shaft have non-circular cross sections.

16. The prosthesis as claimed in claim 1, wherein outer surfaces of the half-shells comprise a coating for secondary osseous fixation.

17. The prosthesis as claimed in claim 1, wherein the compressible pad is also secured to the hollow shaft and the stud.

18. An intervertebral disc prosthesis comprising:
   two plate-shaped or cup-shaped rigid half-shells, each of the half shells being configured to be fixed to one of two vertebrae adjacent to an intervertebral disc to be replaced, the two rigid half-shells being disposed on respective sides of a compression pad and affixed thereto; and
   a first of said two half shells comprising, in a central zone thereof, a hollow shaft oriented toward a second of said two half shells, the second half-shell comprising, in a central zone thereof, a stud oriented toward the first half-shell and penetrating into the hollow shaft, the compression pad including a core portion operatively engaged between and in contact with the hollow shaft and the stud and an outer ring portion disposed outwardly of the core portion and of the hollow shaft, wherein the outer ring portion comprises a first surface and a second surface opposed to the first surface, the first and second surfaces of the outer ring portion being respectively affixed to inner surfaces of the two half-shells, wherein the core portion of the compression pad comprises a first material and the outer ring portion of the compression pad comprises a second material, the second material being harder than the first material and being a polycarbonate urethane type material.

19. The prosthesis as claimed in claim 1, wherein the first and second surfaces of the outer ring portion are respectively affixed to inner surfaces of the two half-shells via a mechanical fastener.

20. The prosthesis as claimed in claim 1, wherein the central zones of the two half shells are each defined by perimetric extents that are closer to a relative midpoint of each respective half shell than any edge of each respective half shell.

* * * * *